United States Patent [19]
Mawhirt et al.

[11] Patent Number: 5,518,006
[45] Date of Patent: May 21, 1996

[54] BLOOD SAMPLING DEVICE

[75] Inventors: James A. Mawhirt, Brooklyn, N.Y.;
Catherine M. Cimini, Somerset;
Anthony Kuklo, Bridgewater, both of N.J.

[73] Assignee: International Technidyne Corp., Edison, N.J.

[21] Appl. No.: 287,828

[22] Filed: Aug. 9, 1994

[51] Int. Cl.[6] ............................................. A61B 5/00
[52] U.S. Cl. .......................................... 128/770; 128/763
[58] Field of Search ........................... 128/749, 751,
128/753, 754, 757, 760, 763, 770; 606/181

[56] References Cited

U.S. PATENT DOCUMENTS

| | | | |
|---|---|---|---|
| 3,760,809 | 9/1973 | Campbell, Jr. | 128/770 X |
| 4,627,445 | 12/1986 | Garcia et al. | 128/770 |
| 4,653,513 | 3/1987 | Dombrowski | 128/770 X |
| 4,703,701 | 11/1987 | Rathbone et al. | 128/763 |
| 4,813,426 | 3/1989 | Haber et al. | 128/763 |
| 4,920,977 | 5/1990 | Haynes | 128/770 |
| 4,924,879 | 5/1990 | O'Brien | 128/770 |
| 5,000,167 | 3/1991 | Sunderland | 128/763 |
| 5,029,583 | 7/1991 | Meserol et al. | 128/770 X |
| 5,368,047 | 11/1994 | Suzuki et al. | 128/770 X |

*Primary Examiner*—Sam Rimell
*Attorney, Agent, or Firm*—Plevy & Associates

[57] ABSTRACT

A blood sampling and transferring device including a disposable auto-pricking lancet and a reservoir integrated together for creating a skin incision and collecting a blood sample therefrom in a one-step operation. The reservoir is preferably funnel shaped with a large opening at one end for receiving the blood sample from the patient, and a small opening at the other end which is small enough to prevent unassisted passage of the collected blood therethrough. The blood sample can then be temporarily stored until such time as the sampling device is engaged with a blood testing device that has an aperture to accommodate the small opening of the reservoir and a pump to draw the blood from the reservoir for testing.

18 Claims, 7 Drawing Sheets

BLOOD SAMPLING DEVICE

FIELD OF THE INVENTION

The present invention relates generally to a blood sampling and transferring device for safely producing a skin incision to cause bleeding and collecting a blood sample therefrom.

BACKGROUND OF THE INVENTION

In recent years, a critical need has emerged for safe and reliable methods of extracting and testing blood samples from patients, particularly as a result of the AIDS epidemic. As a result, automatic skin pricking lancet devices have been developed to replace the traditional needle in some applications. These lancet devices generally have an extractable spring loaded blade or dart for pricking the patient's skin upon the pressing of a button, lever mechanism or switch. The blade then automatically retracts back into the device housing thereby preventing the attending physician or nurse from being pricked by the bloody blade. A sample of blood is then extracted from the patient, often by using a small pipette which draws the blood sample by capillary action. Or, the patient may drop a blood sample into a test tube. In any event, the auto-pricking device is designed for a one time use such that the blade, once extracted and retracted, cannot be extracted a second time thereby preventing accidental skin incisions. After each use, the device is usually discarded.

Examples of such prior art auto-pricking devices are found in U.S. Pat. No. 5,133,730 to Biro et al., entitled "Disposable-Retractable Finger Stick Device", and assigned to International Technidyne Corporation, the assignee herein. This patent teaches a disposable auto-pricking device having a lever arm such that when the device is pressed against the patient's skin and the lever arm depressed, a blade rapidly incises the patient's skin at a predetermined depth, and then safely retracts back into the device. This invention, however, is not directed towards efficiently collecting a sample of the patient's blood for further analysis.

U.S. Pat. No. 4,959,196 to C. Moisson, entitled "Device for Blood Sampling and Analysis" discloses an auto-pricking device integral with an assembly for testing the blood sampled to evaluate desired concentrations of substances therein. After the patient's finger is pricked with this device, the patient deposits a drop of blood onto a strip with a reactive agent. The blood is then automatically tested by means of a reflectometer integral with the assembly. While this device thus enables a particular blood test to be quickly performed in a safe manner, it lacks means built into the unit to temporarily store a blood sample to allow the blood sample to be transferred to another, perhaps more sophisticated blood testing apparatus.

There exists in the prior art, a myriad of apparatuses for performing different tests on blood samples. One such apparatus is found in co-pending U.S. patent application Ser. No. 08/359,923, entitled "Portable Prothrombin Time Test Apparatus and Associated Method of Performing a Prothrombin Time Test", by Gavin et al., and assigned to International Technidyne Corporation, the assignee herein. The apparatus disclosed in this patent performs a prothrombin time (PT) test on a sample of blood. Attachable to the apparatus and necessary for its operation is a disposable cuvette having an opening within which a sample of blood is placed. The blood sample is then tested by the apparatus without contacting the blood sample, whereupon the cuvette is disposed of. The preferred testing method requires that the cuvette be attached to the apparatus prior to the blood sample being placed therein. Thus a blood sample could be transferred directly from a patient to the cuvette if the patient is in close proximity to the apparatus. This is not always practical, however, inasmuch as the apparatus may desirably be located in a room separated from the patient. Alternatively, one could utilize an auto-pricking device to create the skin incision, collect the patient's blood sample in a test tube or pipette, and then transfer the blood to the cuvette. The disadvantage with this latter technique is that the treating physician often prefers to create the incision with the auto-pricking device using his right hand while holding the patient's finger with his left hand (or vice versa), then place the auto-pricking device down while picking up the test tube or pipette with his right hand to gather the blood sample. Similarly, a patient using an auto-pricking device in conjunction with a test tube to take his or her own blood sample would also have to separately retrieve the test tube after performing the incision.

Another option for the physician is to hold the auto-pricking device in his right hand while simultaneously holding the test tube or pipette in his left hand during the incising procedure. In this case, the physician must rely on the patient to hold his finger steady or otherwise hold the finger stationary, which is not always practical.

In any case, the pipette or test tubes are stored separately from the auto-pricker which is a significant drawback in terms of logistics.

Thus there is a need for a blood sampling device including an auto-pricking device integrated with a reservoir to enable a physician or patient to safely collect a blood sample without having to retrieve a separate test tube or other blood storage means. There is also a need for the reservoir of such a blood sampling device to have a funnel-like shape with two openings for enabling clean collection of the blood sample and efficient transferring of the sample to a blood analysis apparatus.

It is an object of the present invention to provide a blood sampling apparatus that fulfills the aforementioned needs and overcomes the drawbacks of the prior art.

There is a further need to provide such a blood sampling device that has a substantially flat platform which allows the device to be readily placed at rest after the blood sampling operation. This feature would enable the incision to be given prompt attention after the blood sample is taken, particularly for a patient taking his or her own blood sample.

SUMMARY OF THE INVENTION

The present invention is directed towards a blood sampling and transferring device including a disposable auto-pricking lancet and reservoir means integrated together for creating a skin incision and collecting a blood sample therefrom in an ergonomically efficient manner. The reservoir means is preferably funnel-shaped with a large opening at one end for receiving the blood sample from the patient, and a small opening at the other end which is small enough to prevent unassisted passage of the collected blood therethrough. The blood sample can then be temporarily stored until such time as the sampling device is engaged with a blood testing device that has an aperture to accommodate the small opening of the reservoir means and a pump to draw the blood from the reservoir means for testing.

BRIEF DESCRIPTION OF THE DRAWINGS

For a better understanding of the instant invention, reference is made to the following description of exemplary embodiments thereof, considered in conjunction with the accompanying drawings, in which.

DESCRIPTION OF THE PREFERRED EMBODIMENT

The blood sampling device of the preferred embodiment of the present invention is comprised of an auto-pricking lancet, a receptacle and a reservoir integrated together. Although integrated during the skin pricking and blood collection operation, the three components are preferably detachable to enable the receptacle and reservoir to be re-used if so desired.

Figure 1:
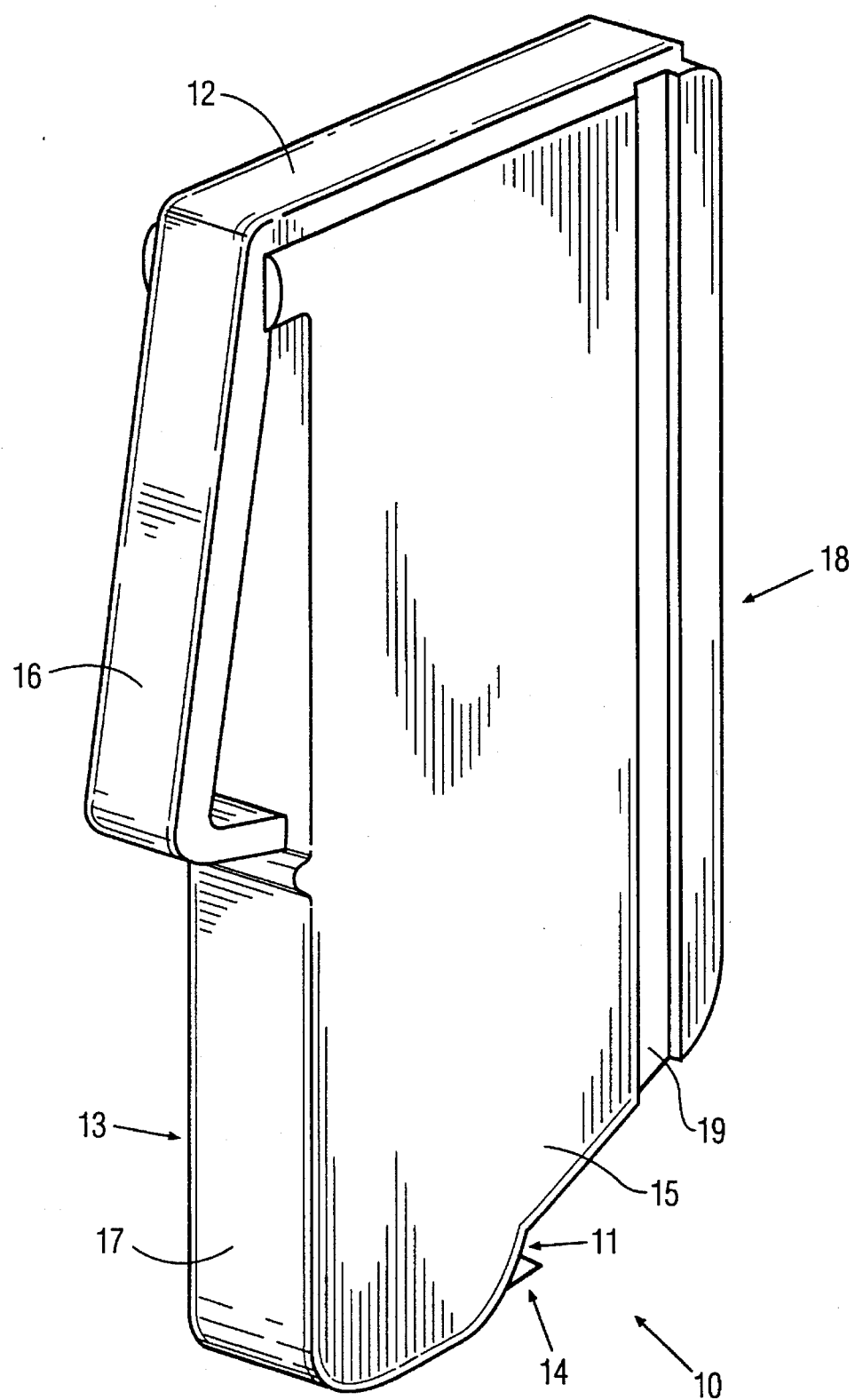
FIG. 1 shows the auto-pricking lancet component of the present invention.

Shown in FIG. 1 is an auto-pricking lancet device 10 particularly adapted for safely pricking a patient's finger such that the treating physician is not at risk of being pricked by a blade contaminated with the patient's blood. The lancet device 10 accomplishes this by employing a lever arm 16 which, when pressed causes a blade 14 to be rapidly extracted and automatically retracted. When the lancet 10 is pressed against a patient's finger and the lever arm 16 is pressed, the blade 14 is automatically extracted to produce an incision, and then automatically retracted back into the lancet housing thereby preventing further undesirable incisions. The lancet 10 is preferably a modified TENDERLETT® lancet, as disclosed by U.S. Pat. No 5,133,730 to Biro et al. entitled "Disposable-Retractable Finger Stick Device", and assigned to International Technidyne Corporation, the assignee herein, the disclosure of which is incorporated herein by reference. It is noted that while the TENDERLETT® lancet is the preferred auto-pricking device, other suitable lancets having retractable blades or darts could also be employed. For instance, lancets employing other manually operated mechanisms such as buttons or switches to perform the function of the lever arm 16 could conceivably be used. In any event, the finger stick device disclosed in the Biro patent may be modified to provide the lancet 10 of FIG. 1 by including a channel 19 on each sidewall 13 and 15. Preferably, the finger stick device of the Biro patent is also modified such that the blade 14 is positioned within the curved area 11 (which is curved to accommodate a human finger), rather than being disposed closer to the front edge 17, as in the cited patent.

Figure 2:
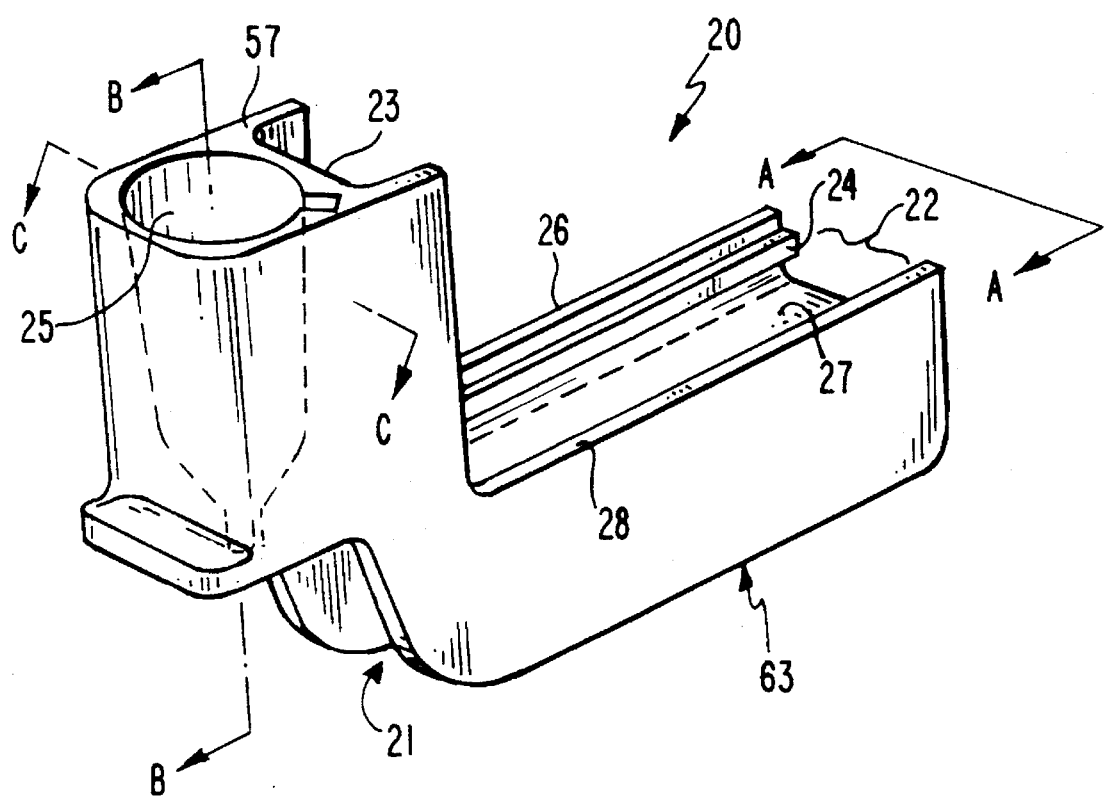
FIG. 2 illustrates the receptacle unit component of the present invention.

The lancet 10 is attachable or adapted to integrate with a receptacle as receptacle 20 of FIG. 2. The exterior dimensions of the lancet 10 and the receptacle 20 are designed to provide an interference fit therebetween. The interference fit affords a firm engagement of the two components. Lancet 10 slides into the channel 22 with the flat rear surface 18 of the lancet 10 abutting flat surface 27 of the receptacle 20. A longitudinal rib 24 protrudes from each sidewall 26 and 28, with the ribs 24 being dimensioned to accommodate the channels 19 as the lancet 10 slides onto the receptacle 20. When fully inserted, the top surface 12 of the lancet 10 will abut the flat receptacle surface 23. (The lancet 10 is shown integrated with the receptacle 20 in FIGS. 6A, 6B, and 8.) Both the lancet 10 and the receptacle 20 preferably have a molded plastic housing for low manufacturing cost and also to allow for a relatively simple interference fit between then. As the two components are integrated together, the plastic of each component flexes to provide the necessary forces to firmly hold them in place. It should be understood that while an interference fit is the preferred attachment means, other attachment means could alternatively be utilized by those skilled in the art, such as push-on locking snaps and so on. Also, the lancet 10 and receptacle 20 could be manufactured as one piece, i.e., unitary.

Figure 3:
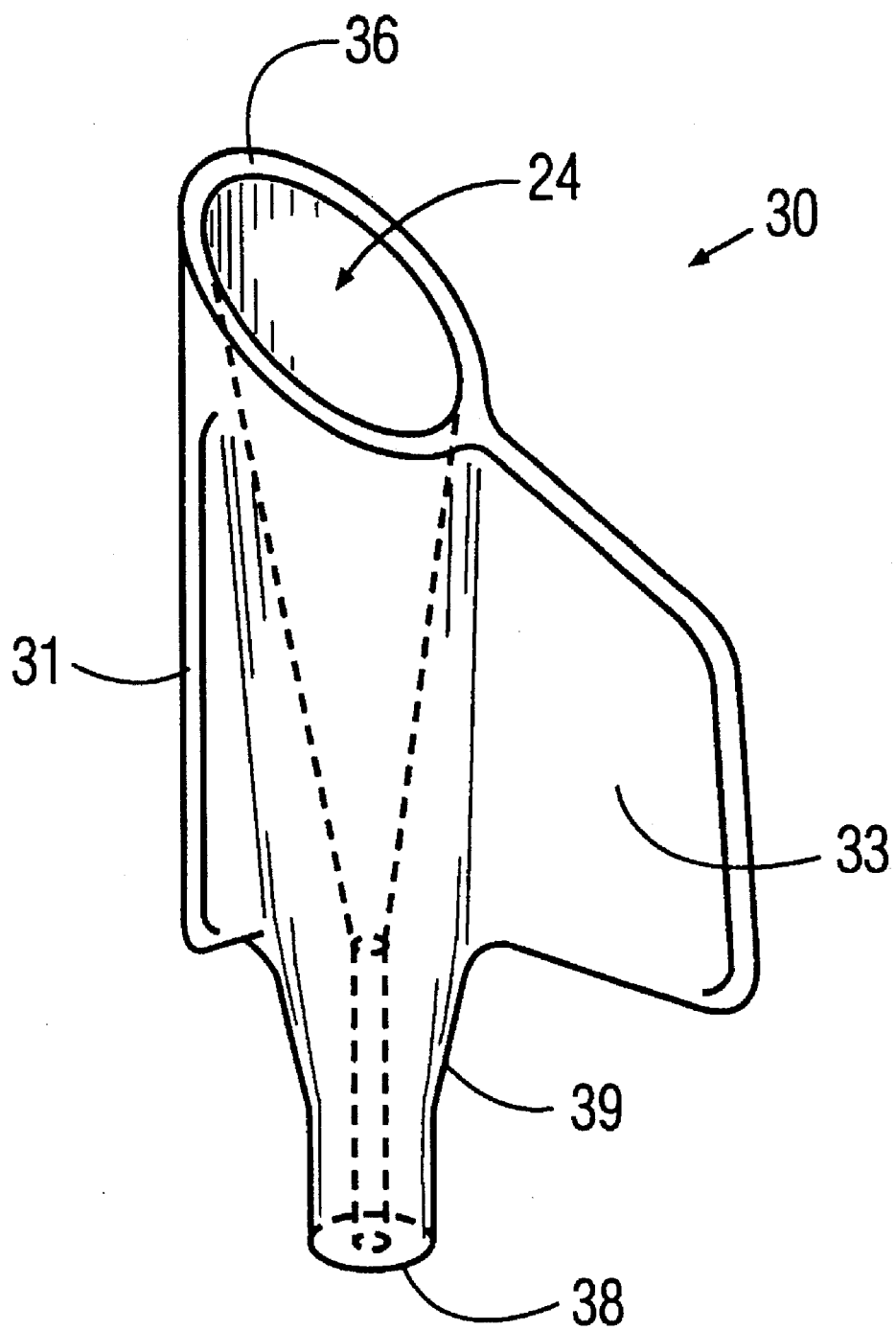
FIG. 3 shows the reservoir unit component of the present invention.

Referring now to FIG. 3, a disposable blood reservoir unit 30 is appropriately dimensioned to fit within the wine glass or funnel-shaped aperture 25 of the receptacle 20. The reservoir 30 has a wine glass or funnel-shaped interior central region that tapers form a large upper opening 36 to a second tapered region 39 to a smaller bottom opening 38. The small bottom opening 38 is narrow enough so that the surface tension of blood dropped into the reservoir aperture 24 prevents the blood from flowing therethrough unassisted. The small bottom opening may have a diameter of, for example, 0.015 in. to accomplish this. The upper opening 36 is preferably angled to facilitate filling of the reservoir. More surface area is thus available for accommodating a given finger with a skin incision, thereby reducing the likelihood of blood missing the reservoir 30. The reservoir 30 preferably has three ribs as rib 33 and two ribs 31 extending radially to firmly hold it in place within the receptacle aperture 25. The three ribs are angularly spaced about 120° from one another. Rib 31 is shown approximately 120° from rib 33; another rib 31, not shown in the figure, is disposed symmetrically between the ribs 33, 31, of FIG. 3, opposite the view shown. It is seen that rib 33 extends radially outward further than rib 31. This is to facilitate manual handling of the reservoir unit 34 by means of rib 33, if so desired.

Figure 4C:
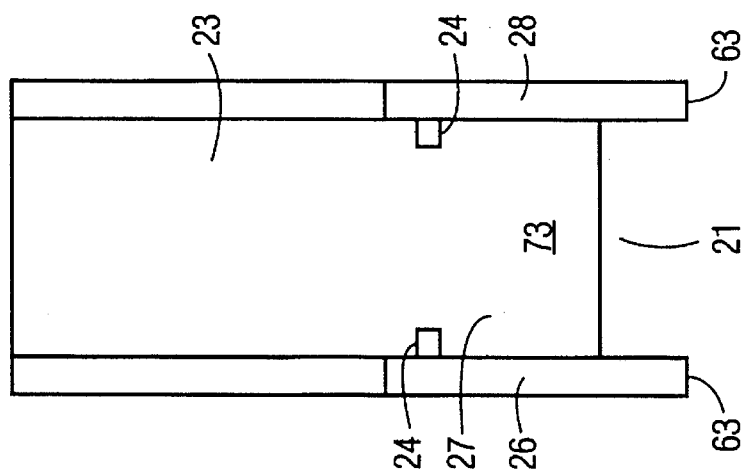
FIG. 4c is the end view AA of FIG. 2.
Figure 4B:
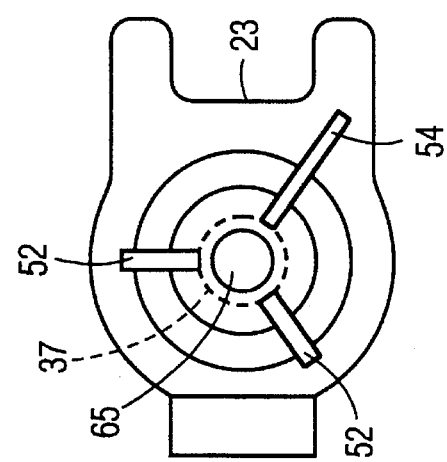
FIG. 4b is the cross-sectional view CC of FIG. 2.
Figure 4A:
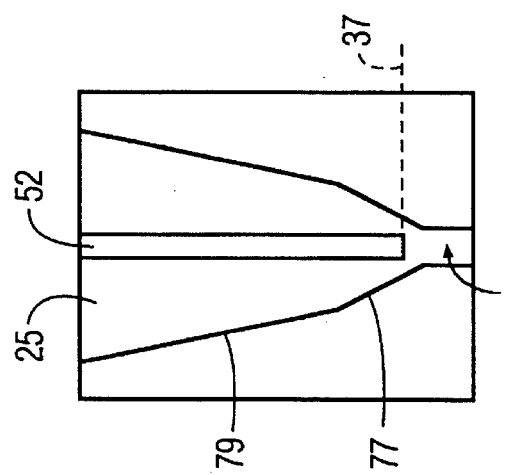
FIG. 4a is the cross-sectional view BB of FIG. 2.

Shown in FIG. 4A is the cross sectional view BB of FIG. 2, showing the inner and outer walls of the portion of the receptacle 20 that accommodates the reservoir unit 30. The aperture 25 preferably matches a predetermined lower portion of the reservoir unit 30. This enables firm engagement by means of an interference fit between the receptacle 20 and reservoir unit 30. In the cross-sectional view BB, one slot 52 is shown which accommodates one of the ribs 31. Slot 52 ends at a predetermined depth level 37. FIG. 4B, which is the cross-sectional view CC of FIG. 2, shows two slots 52 and a longer slot 54, of which both slots 52 and slot 54 extend from depth line 37 to the top of the aperture 25. The three slots are dimensioned to accommodate the reservoir ribs 31, 33. Each rib 31 slides in the corresponding slot 52, and rib 33 slides into slot 54. The bottom of the slots at depth line 37 act as a stop for the reservoir unit. This controls the amount of protrusion of the reservoir unit 30 from the top surface 57 of the receptacle unit 20 when fully inserted therein. Preferably, enough protrusion is provided to allow the top portion of rib 33 to be grabbed to pull the reservoir unit 30 out of receptacle 20 if so desired. The stops 52,54 also serve to control the amount of protrusion of the lower opening 38 of the reservoir 30 from the receptacle 20. Also noted is that tapered region 77 is dimensioned to accomodate tapered region 39 of the reservoir 30; and tapered region 79 is dimensioned to accomodate the tapered region of reservoir 30 between the upper opening 36 and the tapered region 39.

Figure 5:
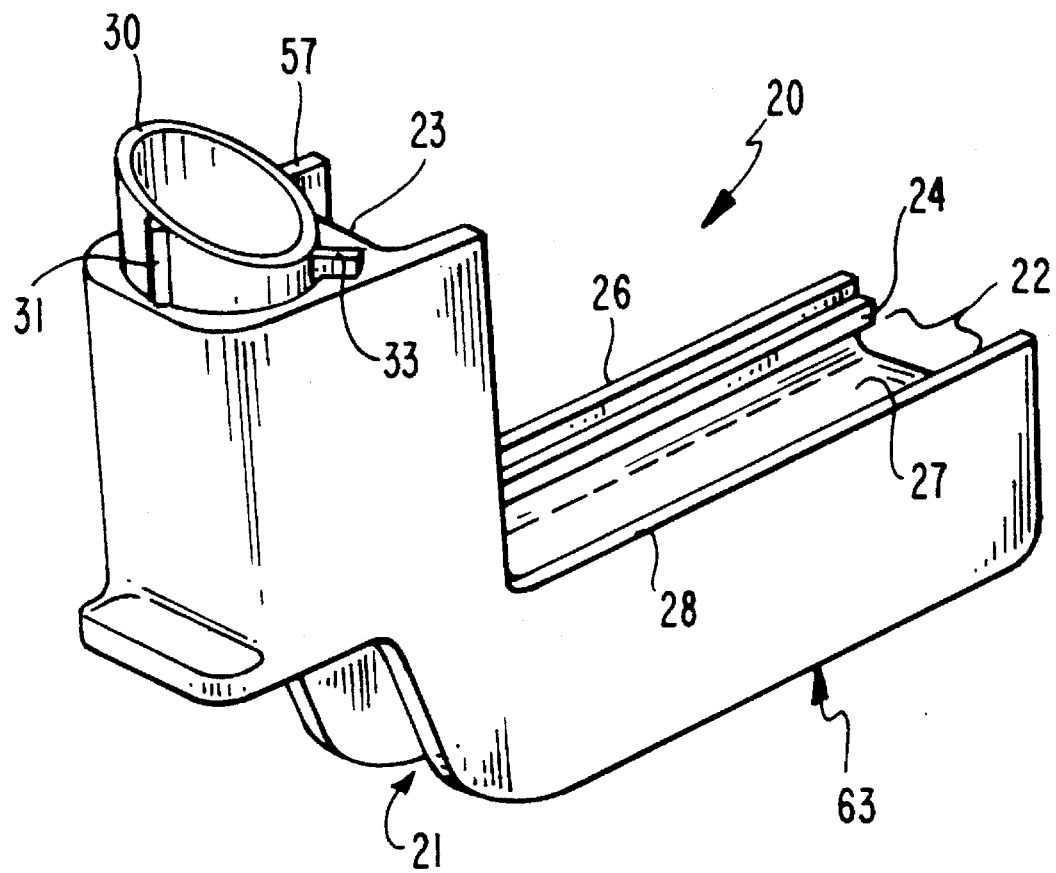
FIG. 5 shows the integration of the reservoir unit with the receptacle unit.

Shown in FIG. 4C is the end view AA of the receptacle 20 of FIG. 2. A solid region 73 having the upper flat surface 27, is disposed between sidewalls 26 and 28. A channel region 21 is thus formed below the solid region 73 and functions to facilitate the attachment of the receptacle 20 to a blood testing device, as will be described. Shown in FIG. 5 is the integration of the reservoir 30 with the receptacle 20. Rib 33 and one of the two ribs 31 are shown inserted in the respective slots of the receptacle 20 described above. Also shown is a flat bottom surface 63 on each sidewall 26, 28. This flat surface 63 acts as a platform and enables the receptacle 20 integrated with the reservoir 30 and lancet 10, to be temporarily placed on a flat surface after a blood sample is placed in the reservoir 30. This allows the patient to immediately attend to his skin incision, if so desired, before transferring the blood sample to a blood testing device.

Figure 6A:
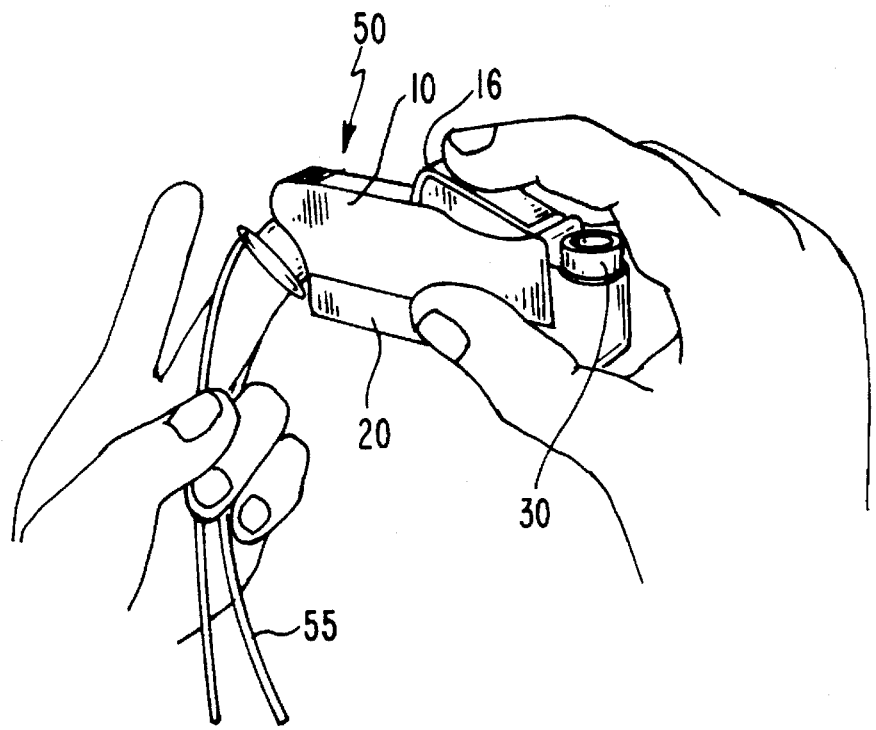
FIGS. 6a and 6b show a method of creating an incision and collecting a blood sample therefrom.
Figure 6B:
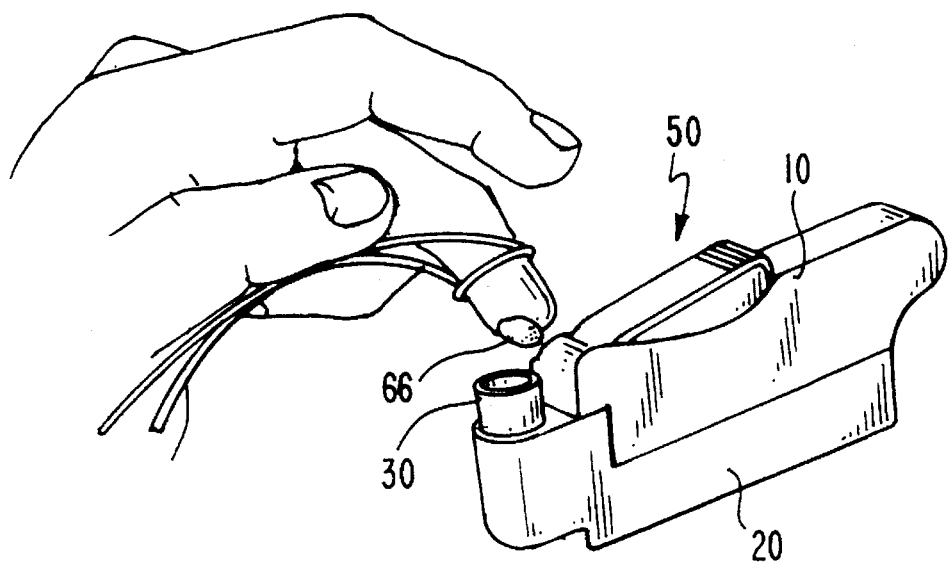
Figure 8:
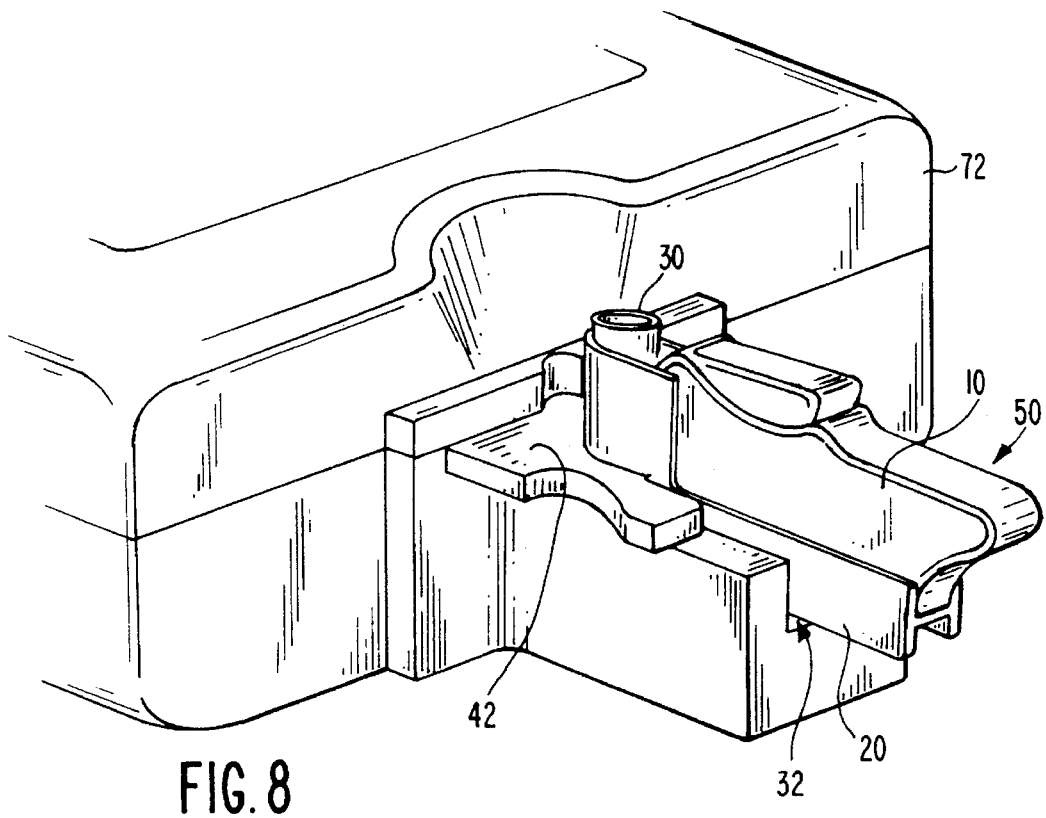
FIG. 8 shows the engagement of the blood testing device with the blood sampling device of this invention.

The lancet 10, receptacle 20 and reservoir unit 30 are shown integrated together in FIGS. 6A, 6B and 8. While the preferred embodiment has described these three components as being manually attachable and detachable by means of interference fits therebetween, it should be understood that the three components could easily be manufactured by one skilled in the art as one disposable, unitary unit. This may be a preferred embodiment for some users and/or manufacturers. Moreover, instead of ribs 31,33 one could thread the outer housing of the reservoir 30 and the inner walls of the receptacle 20 to allow the reservoir 30 to be screwed therein.

Illustrated in FIGS. 6a and 6b is a method for safety creating a skin incision and collecting a blood sample therefrom utilizing the blood sampling apparatus according to the present invention. Referring to FIG. 6a, a blood sampling apparatus 50 comprises the integration of lancet 10, receptacle 20 and reservoir unit 30. A tourniquet 55 such as a rubberband is applied to a patient's finger whereupon the blood sampling device 50 is firmly pressed against the finger and the lever 16 is pressed to create an incision. An initial droplet of blood is wiped clean of the finger, upon which a second droplet of blood is allowed to form. Referring to FIG. 6b, this second droplet of blood 66 is then directed into the reservoir unit 30. Further droplets of blood are allowed to form and are added to the reservoir unit 30 until it is filled to a predetermined level. This predetermined level may be determined by reference to volume level markings inscribed within the reservoir 30. The blood sampling device 50 may then be placed down at rest temporarily on a flat surface while the patient or physician removes the tourniquet and bandages the incision.

Figure 7:
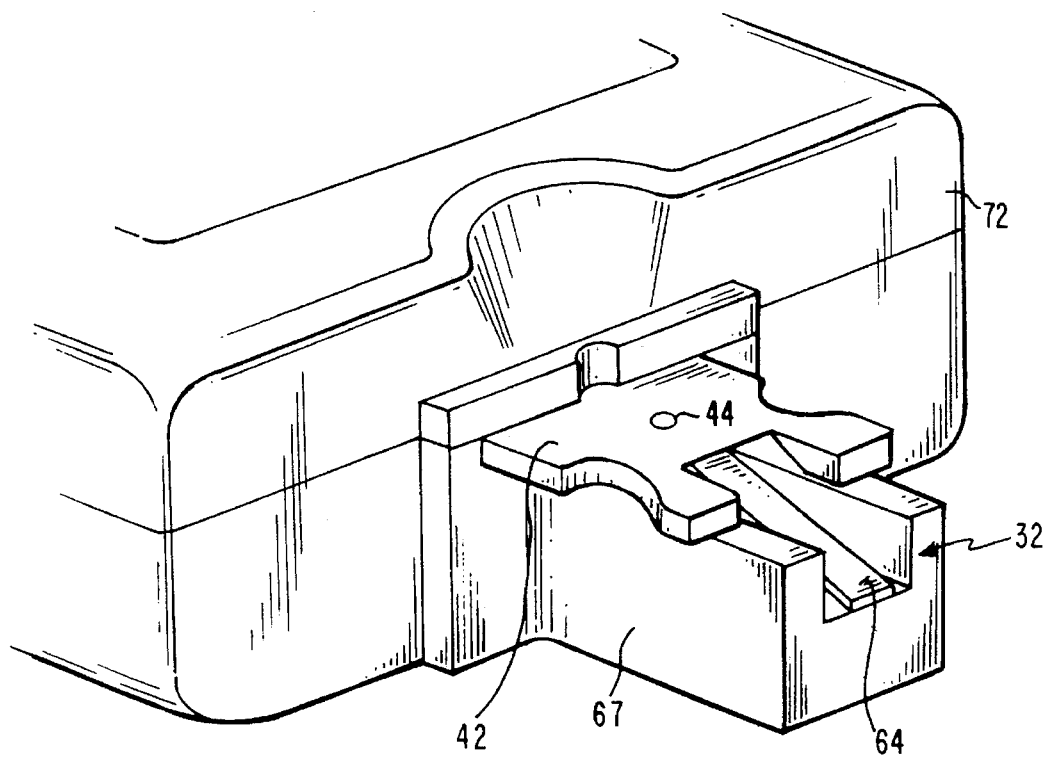
FIG. 7 shows a blood testing device with cuvette adapted to engage with the blood sampling device of this invention.

Referring to FIG. 7, a blood testing device 72 includes an extension 67 having a channel 32 and a central rib 64, dimensioned to accommodate the blood sampling device 50. Inserted into the device 72 is a disposable cuvette 42 which has an aperture 44 for receiving blood. As shown in FIG. 8, the blood sampling device 50 slides into the channel 32. When device 50 is inserted, the lower opening 38 of the reservoir unit 34 aligns over and engages the aperture 44. The aperture 44 may have a rubberized receptacle therewithin to facilitate this engagement. Also, the cuvette 42 may flex up and down when inserted in the testing device 42. The cuvette 42 may then be flexed down in order to engage the blood sampling device 50. The blood in the reservoir unit 30 can then be drawn into the cuvette 42 by a pneumatic pump within the testing device 72. The cuvette 42 has a plurality of conduits therewithin, through which the blood drawn from the reservoir unit 30 travels to a location where it is analyzed. An example of a blood testing device and cuvette adapted to draw blood for testing in this manner can be found in co-pending U.S. patent application Ser. No. 08/327,320 entitled "Portable Prothrombin Time Test Apparatus and Associated Method of Performing a Prothrombin Time Test", by Gavin et al., and assigned to International Technidyne Corporation, the assignee herein.

Thus disclosed is a disposable blood sampling and transferring device for safely creating a skin incision and collecting a sample of blood therefrom in a one step operation. A key advantage of the invention over devices of the prior art is that the invention integrates an auto-pricking lancet with a reservoir for receiving the blood, thereby eliminating the need to retrieve a separate test tube or pipette for the blood collection. Another advantage is that the reservoir has a second small opening for preventing the collected blood from seeping therethrough unassisted. This enables the blood to be drawn from the reservoir by a pneumatic pump in a blood testing device when the blood sampling device is engaged with the testing device.

It should be understood that the embodiment described herein is merely exemplary and that a person skilled in the art may make many variations and modifications to the described embodiment utilizing functionally equivalent components to those described. For example, although the preferred embodiment has described a blood sampling and transferring device which is constructed from three attachable components, one skilled in the art could alternatively manufacture the device as one inseparable unit. Moreover, while an auto-pricking lancet device is preferred, a lancet device that does not include an automatic pricking mechanism could be utilized, coupled or unitary with the reservoir described above, to realize some of the aforementioned benefits of such a combination. Thus, a patient taking his or her own blood sample would not be as much concerned with further accidental pricks and could then realize all of the other aforementioned advantages of the blood sampling apparatus at a lower unit cost. All such variations and modifications are intended to be included within the scope of this invention as defined by the appended claims.

What is claimed is:

1. A blood sampling apparatus for collecting and storing a blood sample from a patient for subsequent transfer to an external blood receiving means, said blood sampling apparatus comprising:

a lancet device for creating a skin incision on the patient to cause bleeding, wherein said lancet device is an auto-pricking lancet device including a housing, a blade and means for extracting said cutting instrument from said housing responsive to a manual operation, whereupon said cutting instrument automatically retracts back into said housing; and reservoir means coupled to said lancet device for collecting a droplet of the patient's blood formed on the patient's skin from the skin incision, said reservoir means having a first opening through which the blood droplet can be placed into said reservoir means and a second externally accessible opening through which blood can be drawn from said reservoir means to the external blood receiving means.

2. The blood sampling apparatus of claim 1, further including means associated with said reservoir means and said lancet device for selectively attaching said reservoir means to said lancet device.

3. The blood sampling apparatus of claim 1, wherein said reservoir means is unitary with said lancet device.

4. The blood sampling apparatus of claim 1, wherein said second opening prevents the unassisted flow of blood therethrough due to the surface tension of the blood in said reservoir means.

5. The blood sampling apparatus of claim 1, further including a receptacle unit, means associated with said receptacle unit and said lancet device for selectively attaching said receptacle unit to said lancet device and means associated with said reservoir means and said receptacle unit for selectively attaching said receptacle unit to said reservoir means wherein said reservoir means is coupled to said lancet device via said receptacle unit.

6. The blood sampling apparatus of claim 5, wherein said receptacle unit is selectively attachable to said lancet device by means of an interference fit therebetween.

7. The blood sampling apparatus of claim 1, wherein said blade automatically and permanently retracts back into said housing following said extraction of said blade, said auto-pricking lancet thereby being adapted for a one time only cutting operation.

8. The blood sampling apparatus of claim 1, wherein said reservoir means includes a tapered region wherein said first opening is defined by a widest section of said tapered region to facilitate filling of said reservoir means.

9. The blood sampling apparatus of claim 1, further including a blood testing device coupled to said blood sampling apparatus and having an aperture to receive blood from said blood sampling device via said second opening.

10. The blood sampling apparatus of claim 9, wherein said testing device includes a pneumatic pump for drawing blood from said reservoir means of said blood sampling apparatus.

11. An apparatus for creating a skin incision on a patient and collecting a sample of blood therefrom, comprising:

a lancet device including: a housing; a cutting instrument; means for extracting said cutting instrument from said housing responsive to a manual operation; and means for automatically retracting said cutting instrument back into said housing, wherein said extracting of said cutting instrument is capable of creating said skin incision thereby causing a droplet of blood to form on the skin of the patient;

a receptacle means;

means associated with said receptacle means and said lancet device for selectively attaching said lancet device to said receptacle means;

a reservoir means;

means associated with said reservoir means and said receptacle means for selectively attaching said reservoir means to said receptacle means, said reservoir means thereby being coupled to said lancet device, said reservoir means having a first opening through which said droplet of blood from said skin incision can be placed into said reservoir means and a second opening through which blood can be drawn from said reservoir means, said second opening preventing the unassisted flow of blood therethrough.

12. The blood sampling apparatus according to claim 11, wherein each of said lancet device, said receptacle means and said reservoir means has a housing, said receptacle means is selectively attachable to respective said lancet device and said reservoir means by means of respective interference fits between said housings.

13. The blood sampling apparatus according to claim 12, wherein said reservoir means has a plurality of longitudinal ribs radially extending therefrom, said ribs enhancing said interference fit between said reservoir means and said receptacle means.

14. The blood sampling apparatus according to claim 13, wherein said receptacle means includes a plurality of channels, each for accepting a respective one of said ribs upon attachment of said reservoir means to said receptacle means, each of said channels having a stop to enable a predetermined protrusion of said reservoir means from said receptacle means upon the attachment thereof.

15. A method of collecting a blood sample from a patient for testing, comprising the steps of:

providing a blood sampling device comprising a lancet device coupled to reservoir means externally of said blood sampling device;

pricking the skin of the patient with the blood sampling device to create a skin incision and cause bleeding, wherein said skin incision is created by pressing said lancet device against the skin of the patient and pressing a lever mechanism of said lancet device thereby causing a blade to be extracted from a housing of said lancet device to create said incision, said blade then automatically retracting back into said housing; and placing a droplet of blood formed on the patient's skin from said skin incision into said reservoir means.

16. The method according to claim 15, further including the step of transferring the blood droplet to a blood testing device by attaching said blood sampling device to said blood testing device, whereby said blood testing device draws the blood from said reservoir means and a test is performed on the blood.

17. The method according to claim 15, wherein said step of placing a droplet of said blood into said reservoir means includes placing the skin with the skin incision in proximity to a first opening of said reservoir means and dropping said blood droplet therein; and further including the step of temporarily storing said blood droplet therein, said reservoir means enabling said temporary storing by including a second opening coupled to said first opening, and preventing the unassisted passage of blood therethrough.

18. The method according to claim 17, further including the steps of:

transferring said blood droplet to a blood testing device by attaching said blood sampling device thereto and aligning said second opening with an aperture of said blood testing device, said aperture adapted for receiving blood, whereupon said blood testing device draws blood from said reservoir means;

performing a test on said blood drawn from said reservoir means;

detaching said blood sampling device from said blood testing device; and disposing of said blood sampling device.

\* \* \* \* \*